| United States Patent [19] | [11] Patent Number: 4,978,611 |
| Hosoda et al. | [45] Date of Patent: Dec. 18, 1990 |

[54] REAGENTS FOR MEASUREMENT OF IMMUNE COMPLEXES AND METHOD FOR MEASUREMENT OF IMMUNE COMPLEXES BY USE THEREOF

[75] Inventors: Kenji Hosoda, Kawagoe; Hideaki Suzuki, Koganei; Takaharu Kubota, Hino; Kiyoshi Nawata, Hachioji, all of Japan

[73] Assignee: Teijin Limited, Osaka, Japan

[21] Appl. No.: 778,097

[22] Filed: Sep. 20, 1985

[30] Foreign Application Priority Data

Sep. 21, 1984 [JP] Japan ................................ 59-196523

[51] Int. Cl.$^5$ ................ G01N 33/535; G01N 33/564; G01N 33/563
[52] U.S. Cl. ........................................ 435/7; 436/506; 436/507; 436/512; 436/531; 436/513; 436/821; 436/828
[58] Field of Search .............. 436/506, 507, 512, 821, 436/828, 513, 531; 435/7, 18, 28, 21

[56] References Cited

U.S. PATENT DOCUMENTS 4,544,640 10/1985 Soma et al. ........................ 436/506

FOREIGN PATENT DOCUMENTS 119292 9/1979 Japan .
0162056 12/1981 Japan ................................. 436/534

OTHER PUBLICATIONS

Pereira et al., "J. of Immunol.", vol. 125, No. 2 (1980), pp. 763–770.
Colomb et al., "Biochem. J.", vol. 145 (1975), pp. 177–183.

*Primary Examiner*—Christine Nucker
*Attorney, Agent, or Firm*—Sughrue, Mion, Zinn, Macpeak & Seas

[57] ABSTRACT

A reagent for measuring immune complexes fixed with an anti-C3 antibody Facb fragment. By using the reagent, immune complexes existing in the blood serum or body fluid are quantitatively measured.

9 Claims, No Drawings

REAGENTS FOR MEASUREMENT OF IMMUNE COMPLEXES AND METHOD FOR MEASUREMENT OF IMMUNE COMPLEXES BY USE THEREOF

BACKGROUND OF THE INVENTION

The present invention relates to a reagent for measuring immune complexes fixed with an anti-C3 antibody-Facb fragment, useful for the quantitative measurement of immune complexes (antigen antibody complexes) which exist in the blood, blood plasma, or other body fluids of a patient suffering from an immune complex disease, and also to a method of immunologically measuring immune complexes by use of the reagent.

Immune complex diseases can be classified into two categories of diseases: one resulting from such an endogenous autoantigenic causation as rheumatoid arthritis (RA), systemic lupus erythematosus (SLE), chronic glomerulonephritis, and tumor, and the other resulting from such an exogenous antigenic causation as acute glomerulonephritis and leukemia. The formation of an immune complex is one of the defense reactions which take place in living body and the immune complex is taken in the reticuloendothelial cells or other phagocytes to be quickly disposed of after its formation in a healthy body. But once the antigenic stimulation continues so long as to cause the mass formation of immune complexes or to allow the formed immune complexes to behave beyond control of the reticuls-endothelial system, etc., they start settling themselves in the blood, blood serum, or body fluid, and finally deposit on the tissue, thus leading it to histological destruction. Therefore, the quantitative measurement of immune complexes existing in the blood, blood serum, or body fluid provides important and useful information in making a diagnosis and setting up a proper method of medical treatment.

Various methods are presently known for quantitatively measuring immune complexes existing in the blood and body fluid and they may fall into two groups, i.e., methods which are conducted physiochemically and those which are based on biologically characteristic factors as shown below.

1. Physiochemical methods

Analytical ultracentrifugation; sucrose density gradient centrifugation; gel filtration; ultrafiltration; electrophoresis; PEG precipitation; low temperature precipitation

2. Methods based on biological characteristics of immune complexes (a) Techniques by use of complement Clq precipitation; Clq-PEG precipitation; Clq deviation test; Clq solid-phase method; C3 sedimentation assay; Kg solid-phase method; anti-C3-F(ab')$_2$ solid-phase method.

(b) Anti-globulin techniques pRF method; mRF method.

(c) Techniques by use of cells

Blood platelet agglutination test; human red blood cell rosette formation test.

The aforementioned physiochemical methods, however, have a demerit of showing a low degree of singularity and the methods based on biological characteristics have problems in that they involve the difficulty of obtaining the material protein and that they lack in stability. Of these methods, the anti-C3-F(ab')$_2$ solid-phase method may be a comparatively good one; however, this method still involves the following problem.

The anti-C3-F(ab')$_2$ solid-phase method (Pereira, A. B., J. Immunol. 125, 763–770) (Japanese Patent Application Laid-open No. 500207/82) is widely practiced in detecting immune complexes linked with C3 because of the ready availability of anti-C3 on the market. This method uses F(ab')$_2$ fragment of anti-C3 antibody in order to keep the measurement system free from the mixing up with a rheumatoid factor (RF) (i.e. RF links with Fc); however, the method has a fault in that the measurements are often found somehow modified by the pepsin agglutinator (an auto-antibody which recognizes F(ab')$_2$) (Osterland, C. K. Vox Sang., 8; 133; 1963) which is an auto-antibody existing in the blood serum of a patient with RA, SLE, etc.

SUMMARY OF THE INVENTION

As the result of a strenuous research work made in an effort to develop a method of specifically determining the quantity of immune complexes in view of the present situation mentioned above, the inventors of the present invention have found that the mixing up of RF and pepsin agglutinator existing in the blood serum of a patient can be eliminated by use of Facb fragment from which CH3 domain of anti-C3 antibody is removed (see M. Colomb, R. R. Porter, Biochem. J., 145; 177 (1975)), thus making it possible to specifically determine the quantity of immune complexes.

The present invention is directed to a standard material for measuring immune complexes fixed with an anti C3-antibody-Facb fragment-, and a method of quantitatively measuring immune complexes existing in the blood serum or body fluid, which method comprises allowing a reagent fixed with an anti-C3 antibody-Facb fragment to contact the human blood serum or body fluid, and then making the immune complexes, which are thus linked with the reagent, react with enzyme-labeled, or radiolabeled, or fluorescence-labeled anti-immunoglobulin antibody or staphylococcus protein A (which recognizes Fc).

DESCRIPTION OF THE PREFERRED EMBODIMENTS

The anti-C3 antibody which is used for obtaining the anti-C3 antibody-Facb fragment proposed in the present invention is an immunoglobulin fraction obtained by immunizing a rabbit, goat, sheep, horse, rat, mouse, swine, etc. with human C3, or human C3 fraction, or other animal's C3, or its C3 fraction. Rabbit immunoglobulin G obtained by immunization with human C3 is especially desirable. What is referred to as the C3 fraction includes C3a, 3b, 3c, 3d, and still minor fractions having immunogenecity. Also monoclonal antibody can be used as anti-C3 antibody.

Anti-C3 antibody-Facb fragment are obtained in the following manner.

Firstly an immunoglobulin fraction of anti-C3 antibody is prepared and treated with acid. The treated product is then hydrolyzed with the use of such proteolytic enzymes as plasmin and trypsin. Thereafter, the hydrolysis product is refined by means of gel filtration, ion exchange, electrophoresis, chromatofocusing, and affinity column on protein A fixed Sepharose 4B to obtain anti-C3 antibody-Facb fragment with CH3 domain of anti-C3 antibody removed therefrom.

To make thus obtained anti-C3 antibody-Facb fragment into a measuring reagent, it is fixed to an appropriate carrier. The fixing work can be carried out according to a known method. As the carrier, solid phase balls, beads, gears, tubes and microplates made from polystyrene, polyethylene, polyacrylate, Teflon, polyacetal, polyvinyl chloride . etc., for instance, are desirably used.

Since the fixed anti-C3 antibody-Facb fragment of the present invention operates against the participation of a rheumatoid factor and pepsin agglutinator existing in the blood, blood serum, or body fluid of a patient of immune complex diseases in the measurement system and reacts specifically with immune complexes, it is very useful for the quantitative measurement of immune complexes.

One of the reasons why anti-C3 antibody-Facb fragment of the present invention does not react with a rheumatoid factor is believed to be attributable to the fact that the recognizing part on the immunoglobulin G of rheumatoid factor is at the juncture of the CH3 domain or CH2-CH3 domain of IgG and that anti-C3 antibody-Facb fragment has no such part in its structure.

Also, one of the reasons that anti-C3 antibody-Facb fragment does not react with pepsin agglutinator is assumed to be attributable to the fact that the recognizing part on the immunoglobulin G of pepsin agglutinator makes a newly formed section (a section on F(ab')$_2$) subsequent to the severance of immunoglobulin G by pepsin, or a newly formed stereosructure, and that Facb has a structure at the section apparently different from that of F(ab')$_2$.

Accordingly, a reagent for the measurement of immune complexes which has anti-C3 antibody-Facb fragment as a component part and a method for measuring immune complexes by use of it are proposed according to the present invention.

The proposed method for the measurement of immune complexes comprises fixing anti-C3 antibody-Facb fragment preferably to solid phases, causing a mutual reaction between thus fixed ones and immune complexes existing in the specimen of human serum or body fluid, and determining the quantity of immune complexes, which are linked to the solid phases by the reaction between the C3 part of an immune complex and anti-C3 antibody-Facb fragment, by the second reaction of the anti-immunoglobulin antibody, or staphyloccus protein A, labeled with a radioactive substance, or enzyme, or fluorescent material which links with immunoglobulin in the immune complex. As the labeling material, it is a usual practice to use such enzymes as horseradish peroxidase, $\beta$-D-galactosidase, and alkaline phosphotase in the methods where enzymes are used (EIA); $^{125}$I, $^3$H, etc. in the methods where radio-active substances are used (RIA); and fluorescein isothiocyanate, etc. are used in the methods where fluorescent materials are used (FIA, however, any other materials may be used so far as the activity of the labeling materials is measurable.

In cases where the labeling material is an enzyme, a substrate is used to measure its activity. As examples of the substrate, 2,2'-azinodi-(3-ethylbenzthiazolinesulphonic acid (6)) ammonium salt (ABTS)-H$_2$O$_2$, 5-amino salicylic acid-H$_2$O$_2$, O-phenylenediamine-H$_2$O$_2$, 4-aminoantipyrine, etc. may be mentioned as the substrate for horseradish peroxidase, and fluorescein-di-($\beta$-D-galactopyranoside), O-nitrophenol-$\beta$-D-galactopyranoside, etc. may be mentioned as the substrate for $\beta$-D-galactosidase. In carrying out the measurement, publicly known reagents such as solubilizer, detergent, and reaction terminator are used in addition to the aforementioned reagents.

The present invention will be illustrate, but is not intended to be limited, by the following examples.

EXAMPLE 1

(1) Preparation of rabbit anti-(human C3) antibody-Facb fragment

A W/O emulsion was prepared by mixing C3 obtained from human blood plasma with purification and complete Freund's adjuvant at the ratio of 1:1 and rabbits were immuned to 2 ml of thus prepared W/O emulsion two weeks apart. Ten days after the fourth immunization, the whole blood was drawn from the rabbits to collect anti-serum. After an equal amount of PBS was added to the collected anti-serum, saturated ammonium sulfate double in amount was added thereto little by little and had the precipitate centrifuged, which was then redissolved in PBS. The solution was dialyzed against 0.01M PB (PH 8.0) and passed through a column of DEAE equilibrated with 0.01M PB to obtain IgG fractions (rabbit anti-human C3)-IgG).

2 ml of IgG fraction (5 mg/ml) was adjusted to pH 2.5 by use of 1 NHCl and incubated at 30° C. for minutes. The pH value of the solution was raised back to 7.0 by use of 1NNaOH and immediately thereafter 5 casein unit of plasmin was added and allowed to undergo the reaction for 10 minutes at 30° C. Immediately after the reaction was over, the reaction mixture was cooled in an ice bath and plasmin was removed on a column of lysine Sepharose and unreacted IgG was removed on a column of protein A Sepharose. The reaction product was dialyzed for a whole day and night against PBS at 4° C. to obtain anti C3 antibody-Facb fragment.

(2) Preparation of immunoassay reagent (2-1) Method for fixing anti-C3 antibody-Facb fragment to balls or plates The anti-(human C3) antibody-Facb fragment obtained rn the aforementioned (1) was adjusted to have protein concentration of 30 $\mu$g/ml by use of phosphate buffered saline solution (PBS) and polystyrene balls were immersed in the solution for 3 whole days to obtain polystyrene balls fixed with anti-(human C3) antibody-Facb fragment. The balls were then placed in a 0.5% BSA-PBS solution for a whole day and night.

The anti-(human C3) antibody-Facb fragment obtained in the aforementioned (1) was adjusted to have protein concentration of 20 $\mu$g/ml by adding 0.1M carbonate buffer (pH 9.6), and 200 $\mu$l/well of the adjusted solution was put into microplates for EIA use. After this 3-day immersion was over, microplates fixed with anti-(human C3) antibody-Facb fragments were obtained.

(2-2) Preparation of other reagents

A substrate solution for HRP (horseradish peroxidase) was made to contain 50 mg/dl of ABTS and 50 $\mu$l/dl of 2M H$_2$O$_2$ in 0.1M phosphate/citrate buffer (pH 4.5).

As a stop solution for HRP, 0.2M oxalic acid was used.

EXAMPLE 2

Measurement of immune complexes of IgA class by EIA

Each 500 μl of a 1/200 solution of blood serum of patients was poured on the polystyrene balls fixed with anti-(human C3) antibody-Facb fragment obtained in Example 1 and the reaction was allowed to go on at 37° C. for 1 hour. After the balls were washed with PBS, anti-(human IgA) labeled with HRP was added thereto and allowed to undergo the reaction at 37° C. for 1 hour. After washing, the balls were made to develop color by addition of 400 μl of a substrate solution for HRP at 37° C. for 30 minutes, at the end of which the reaction was terminated by use of a stop solution. The immune complexes existing in the blood serum were then measured quantitatively by using a chemical conjugate of human IgA and human C3 as the standard material for calibration curve. Also, measurements were made at the same time by use of balls fixed with anti(human C3)-F(ab')₂ and with anti-(human C3)-IgG.

The results of measurements made with the blood sera of the respective patients are shown in Table 1. As shown in Table 1, it is clear that the values are largely modified by the effect of pepsin agglutinator in the method of using anti-C3-F(ab')₂, and also the values are largely modified by the effect of RF in the methodfusing anti-C3-IgG. And it is clear that in the method of fixing anti-C3-Facb according to the present invention the modification of measurements resulting from the application of RF or pepsin agglutinator is avoided. In the case of negative of both RF and pepsin agglutinator, the correct measurements can be attained by any method as shown in Table 1.

TABLE 1

|  | Patient | Anti-C3-Facb | Anti-C3-F(ab')₂ | Anti-C3-IgG |
|---|---|---|---|---|
| Rhuematoid | A | 3.2 μg/ml | 5.8 μg/ml | 76.0 μg/ml |
| factor | B | 6.5 | 7.1 | 35.5 |
| Positive | C | 5.0 | 5.5 | 18.5 |
| (React with IgG) | D | 2.5 | 3.1 | 12.8 |
| Pepsin | E | 3.7 | 100.0 | 4.0 |
| agglutinator | F | 10.5 | 55.1 | 9.6 |
| Positive | G | 2.9 | 21.1 | 3.2 |
| (React with F(ab')₂) | H | 3.2 | 16.8 | 3.5 |
| IgA-immune | I | 6.6 | 6.5 | 7.2 |
| complex | J | 9.3 | 9.2 | 10.2 |
| Positive | K | 7.2 | 7.8 | 7.5 |
|  | L | 15.0 | 13.8 | 15.3 |
| Healthy | M | 2.0 | 1.5 | 1.8 |
| normal man | N | 2.9 | 2.5 | 3.1 |
| (below about | O | 2.6 | 2.3 | 2.1 |
| 3 μg/ml) | P | 2.4 | 3.1 | 2.4 |

EXAMPLE 3

Preparation of rabbit anti-(human C3b) antibody-Facb fragment

A rabbit anti-(human C3b) antibody was prepared by immunizing rabbits according to the method of Example 1 by use of C3b, which had been prepared after the method proposed by J. O. Minta et al. (J. Immunol. 118; 2192 (1977)), as an antigen and was further subjected to the enzymatic digestion treatment to give rabbit anti-(human C3b) antibody-Facb fragment. Polystyrene balls for use as the standard materials for measurement of immune complexes were prepared therefrom according to the same method as described in Example 1.

EXAMPLE 4

Measurement of immune complexes of IgG class by use of RIA

Each 500 μl of a 1/200 PBS solution of blood serum of patients was added to the polystyrene balls fixed with anti-(human C3b) antibody-Facb fragment obtained in Example 3 and the reaction was carried on at 37° C. for 1 hour. After washing with PBS, anti-(human IgG) labeled with $^{125}I$ was added thereto and the mixture was allowed to undergo the reaction at 37° C. for 1 hour. After washing of the balls, the immune complexes were quantitatively measured with a γ-counter by using thermally coagulated IgG as the standard material for calibration curve. For comparison's sake, experiments were made at the same time by use of balls fixed with anti-(human C3)-F(ab')₂ and with anti-(human C3)-IgG.

The results of measurements made o the blood sera of the respective patients are shown in Table 2. As seen from Table 2, it is clear that the method of fixing anti-C3-Facb proposed by the present invention is free from the modification of measurements resulting from the use of RF or pepsin agglutinator.

TABLE 2

|  | Patient | Anti-C3-Facb | Anti-C3-F(ab')₂ | Anti-C3-IgG |
|---|---|---|---|---|
| Rheumatoid | a | 9.2 μg/ml | 8.9 μg/ml | 15.4 μg/ml |
| factor | b | 1.8 | 2.0 | 5.2 |
| Positive | c | 12.1 | 11.5 | 18.0 |
|  | d | 18.3 | 18.6 | 52.0 |
| Pepsin | e | 13.5 | 45.3 | 14.6 |
| agglutinator | f | 3.2 | 30.7 | 3.3 |
| Positive | g | 5.5 | 11.8 | 6.0 |
|  | h | 2.4 | 9.5 | 2.1 |
| Immune | i | 16.9 | 17.5 | 17.5 |
| Complexes | j | 8.3 | 8.8 | 8.3 |
| Positive | k | 5.3 | 6.0 | 5.1 |
|  | l | 15.5 | 15.2 | 14.8 |
| Healthy | m | 1.8 | 1.7 | 2.3 |
| normal man | n | 1.5 | 1.5 | 1.4 |
| (below about | o | 2.5 | 3.0 | 3.2 |
| 3 μg/ml) | p | 2.1 | 2.3 | 1.6 |

EXAMPLE 5

Preparation of rabbit anti-(human C3) antibody-Facb fragment

Rabbit anti-(human C3) antibody-Facb fragment was obtained according to the method adopted in Example by using anti-(human C3b) antibody IgG manufactured by DAKO Co. A standard material for the measurement of immune complexes was prepared in the form of a microplate by use thereof according to the same method as Example 1.

EXAMPLE 6

Measurement of immune complexes of IgM class by use of EIA

Each 200 μl of a 1/100 solution of blood serum taken from patients was added to the microplates fixed with anti-(human C3d) antibody-Facb fragment obtained in Example 5 and the two were allowed to react with each other at 37° C. for 1 hour. The microplates were then washed with PBS and anti-(human IgM) labeled with HRP was added to them and were made to undergo the reaction at 37° C. for 1 hour. After washing, the microplates were made to develop color by addition of 200 μl of a substrate solution for HRP et 37° C. for 20 minutes and the measurements were made at 405 nm with the use of a reader for licrolizer. The measurements of immune complexes were conducted by use of a chemical conjugate of human IgM and human C3 as the standard material for calibration curve. As the comparative experiment, measurements were made simultaneously by use of microplates fixed with anti C3-F(ab')2 and also those fixed with anti C3-IgG.

The results of the measurements made on the sera of patients are shown in Table 3. It is clear from what shown in Table 3 that the method of fixing anti-C3d-Facb of the present invention is free from the modification of measurements resulting from RF or pepsin agglutinator.

TABLE 3

|  | Patient | Anti-C3-Facb | Anti-C3-F(ab')2 | Anti-C3-IgG |
|---|---|---|---|---|
| Rheumatoid | 1 | 4.8 μg/ml | 5.1μg/ml | 8.9μg/ml |
| factor | 2 | 4.0 | 3.8 | 13.5 |
| Positive | 3 | 1.5 | 1.2 | 6.2 |
|  | 4 | 16.1 | 15.8 | 38.7 |
| Pepsin | 5 | 2.7 | 30.2 | 3.0 |
| agglutinator | 6 | 9.1 | 27.7 | 9.5 |
| Positive | 7 | 2.0 | 125.0 | 2.3 |
|  | 8 | 2.8 | 12.5 | 3.5 |
| Immune | 9 | 11.8 | 11.0 | 12.5 |
| complexes | 10 | 6.5 | 7.0 | 6.2 |
| Positive | 11 | 8.8 | 8.0 | 8.5 |
|  | 12 | 15.2 | 16.1 | 15.3 |
| Healthy | 13 | 2.2 | 2.9 | 2.6 |
| normal nam | 14 | 2.8 | 2.9 | 2.5 |
| (below about | 15 | 1.9 | 1.7 | 1.7 |
| 3 μg/ml) | 16 | 3.2 | 3.9 | 3.4 |

As the detailed explanation shows in the above, the present invention has for the first time made it possible to make an accurate quantitative measurement of immune complexes existing in the blood serum of a patient eliminating interference of rheumatoid factor and pepsin agglutinator. It has now been made possible to obtain an accurate knowledge on the relationship between the quantity of immune complexes existing in the blood serum, etc. of a patient and the conditions of the disease free from the interfering factors for the benefit of taking an effective measure. It may therefore be said that the present invention is to provide a useful means for the diagnosis and pathological researches of immunologic diseases.

What is claimed is:

1. A reagent for measuring immune complexes which are fixed with an anti-C3 antibody-Facb gragment, said reagent consisting of said anti-C3 antibody-Facb fragment fixed to a carrier.

2. The reagent for measuring immune complexes according to claim 1, wherein said anti-C3 antibody-Facb fragment is an anti-(human C3) antibody-Facb fragment.

3. The reagent for measuring immune complexes according to claim 1, wherein said anti-C3 antibody-Facb fragment is a rabbit anti-(human C3) antibody-Facb fragment.

4. A method of quantitatively measuring immune complexes existing in human blood serum or body fluid and which become fixed with an anti-C3 antibody-Facb fragment, comprising: (1) contacting a reagent consisting of said anti-C3 antibody-Facb fragment fixed to a carrier with the human blood serum or body fluid thereby linking the immune complexes to the anti-C3 antibody-Facb fragment of the reagent, (2) reacting an anti-immunoglobulin antibody labeled with a labeling material or staphylococcus protein A labeled with a labeling material with the immune complexes linked to the reagent; and (3) quantitatively measuring the immune complexes in the human blood serum or body fluid by measuring the activity of the labeling material.

5. The method of claim 4, wherein said anti-C3 antibody-Facb fragment, is an anti-(human C3) antibody-Facb fragment.

6. The method of claim 4, wherein said anti-C3 antibody-Facb fragment is a rabbit anti-(human C3) antibody-Facb fragment.

7. The method of claim 4, wherein said anti-immunoglobulin antibody labeling material is an enzyme, a radioactive substance or a fluorescence substance and said staphylococcus protein A labeling material is a radioactive substance.

8. The reagent for measuring immune complexes according to claim 1, wherein said carrier is one member selected from the group consisting of solid balls, beads, gears, tubes and microplates made from polystyrene, polyethylene, polyacrylate, Teflon, polyacetal, or polyvinyl chloride.

9. The method of claim 4, wherein said carrier is one member selected from the group consisting of solid phase balls, beads, gears, tubes and microplates made from polystyrene, polyethylene, polyacrylate, Teflon, polyacetal, or polyvinyl chloride.

* * * * *